(12) United States Patent
Wu

(10) Patent No.: US 10,684,212 B2
(45) Date of Patent: Jun. 16, 2020

(54) METHOD AND SYSTEM FOR REFERENCE-ASSISTED DROPLET DETECTION, INDEXING AND SORTING FOR ASSAYS AND DIAGNOSTICS

(71) Applicant: Amberstone Biosciences LLC, Cerritos, CA (US)

(72) Inventor: Guikai Wu, Cerritos, CA (US)

(73) Assignee: AMBERSTONE BIOSCIENCES LLC, Cerritos, CA (US)

( * ) Notice: Subject to any disclaimer, the term of this patent is extended or adjusted under 35 U.S.C. 154(b) by 231 days.

(21) Appl. No.: 15/962,317

(22) Filed: Apr. 25, 2018

(65) Prior Publication Data

US 2018/0321130 A1 Nov. 8, 2018

Related U.S. Application Data

(60) Provisional application No. 62/500,249, filed on May 2, 2017.

(51) Int. Cl.

| | |
|---|---|
| *B01L 3/00* | (2006.01) |
| *G01N 33/58* | (2006.01) |
| *G01N 15/14* | (2006.01) |
| *G01N 27/22* | (2006.01) |
| *G01N 27/74* | (2006.01) |
| *G01N 15/10* | (2006.01) |

(52) U.S. Cl.
CPC .... *G01N 15/1459* (2013.01); *B01L 3/502761* (2013.01); *B01L 3/502784* (2013.01); *G01N 15/1484* (2013.01); *G01N 27/22* (2013.01); *G01N 27/745* (2013.01); *G01N 33/58* (2013.01); *B01L 2200/0652* (2013.01); *B01L 2300/0663* (2013.01); *B01L 2400/0415* (2013.01); *B01L 2400/0424* (2013.01); *B01L 2400/0436* (2013.01); *B01L 2400/0439* (2013.01); *G01N 2015/1006* (2013.01); *G01N 2015/149* (2013.01); *G01N 2015/1486* (2013.01)

(58) Field of Classification Search
CPC ..... B01L 2200/0652; B01L 2300/0663; B01L 2400/0415; B01L 2400/0424; B01L 2400/0436; B01L 2400/0439; B01L 3/502761; B01L 3/502784; G01N 15/1459; G01N 15/1484; G01N 2015/1006; G01N 2015/1486; G01N 2015/149; G01N 27/22; G01N 27/745; G01N 33/58
See application file for complete search history.

(56) References Cited

U.S. PATENT DOCUMENTS

| | | | | |
|---|---|---|---|---|
| 2016/0253584 | A1* | 9/2016 | Fodor | G06K 19/06103 235/494 |
| 2016/0298173 | A1* | 10/2016 | Wang | C12Q 1/686 |

* cited by examiner

*Primary Examiner* — Jennifer Wecker
(74) *Attorney, Agent, or Firm* — Han IP PLLC; Andy M. Han

(57) ABSTRACT

Provided are methods and systems for reference object assisted droplet detection, indexing, and sorting in assays and diagnostics. Provided are compositions of reference objects and methods of usages. Provided are systems and exemplary modules and functions for the detection, counting, indexing, data processing, and sorting of reference objects and assay droplets in a microfluidic device. The reference objects may serve as a dynamic micro-scale positioning system for the indexing and sorting of individual assay droplets.

20 Claims, 11 Drawing Sheets

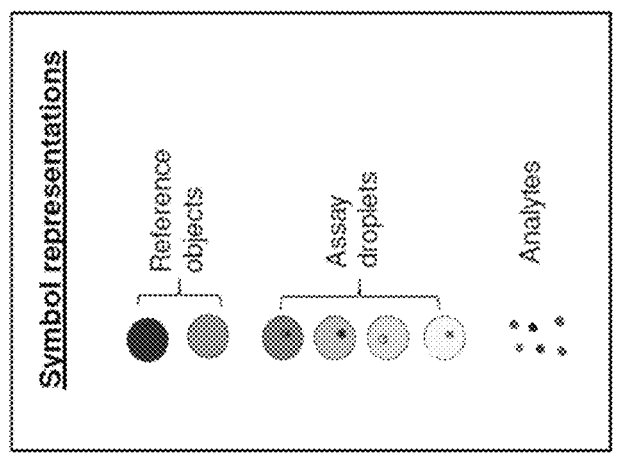
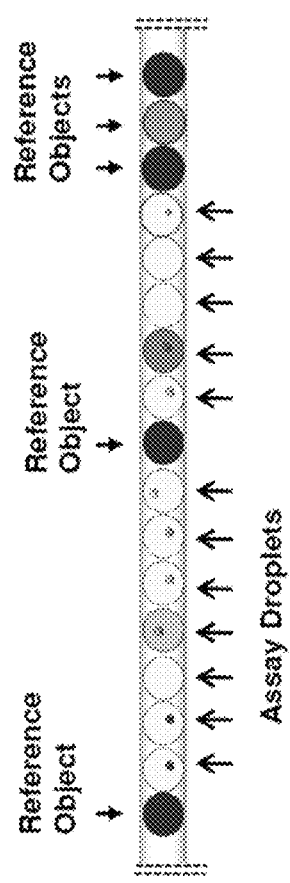
FIG. 1A
FIG. 1B

FIG. 2A

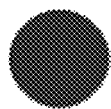 Droplet with soluble reference material (e.g., fluorescent molecule or complex, colored dyes)

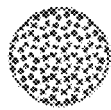 Droplet with insoluble reference material (e.g., fluorescent beads, color-coded particles)

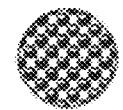 Droplet with other insoluble reference material (e.g., magnetic particles, electrochemical sensors)

FIG. 2B

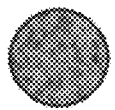 Particle comprising a solid matrix (e.g., alginate or hydrogel) and a reference material (e.g., fluorescent dyes or magnetic particles)

FIG. 2C

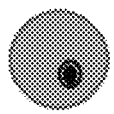 Droplet with both an analyte (e.g., a cell) and a low, distinguishable level of reference material (e.g., a fluorescent dye)

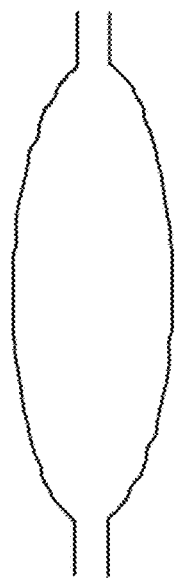
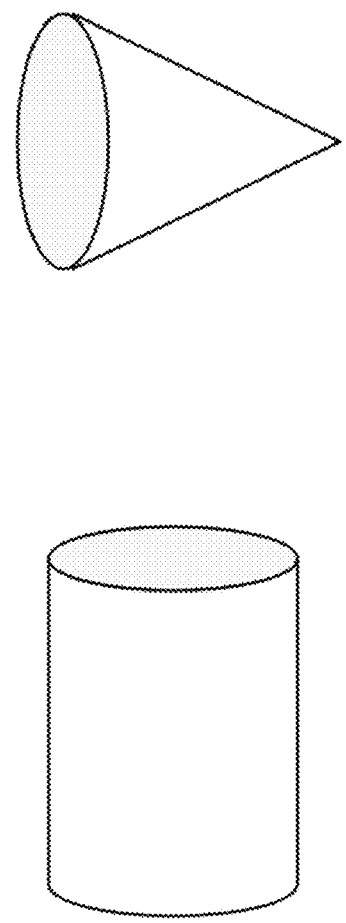
FIG. 4A
FIG. 4B

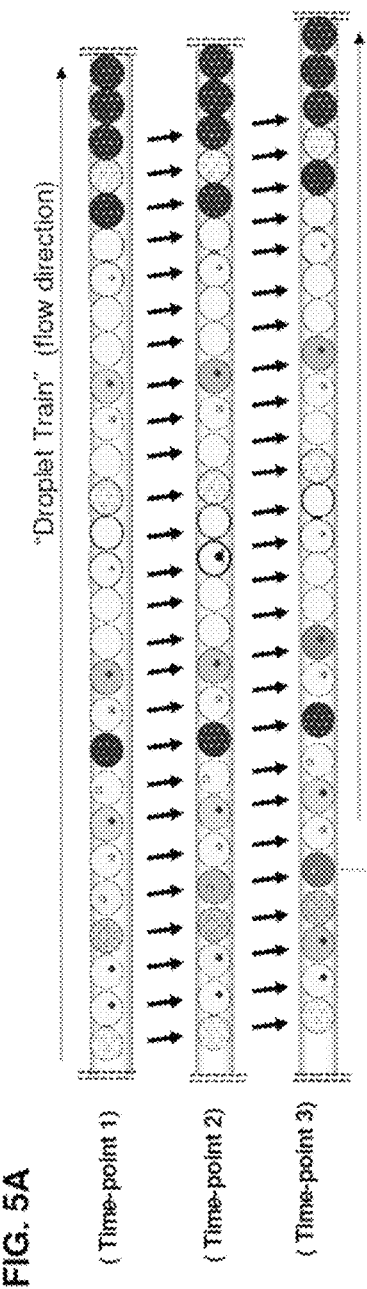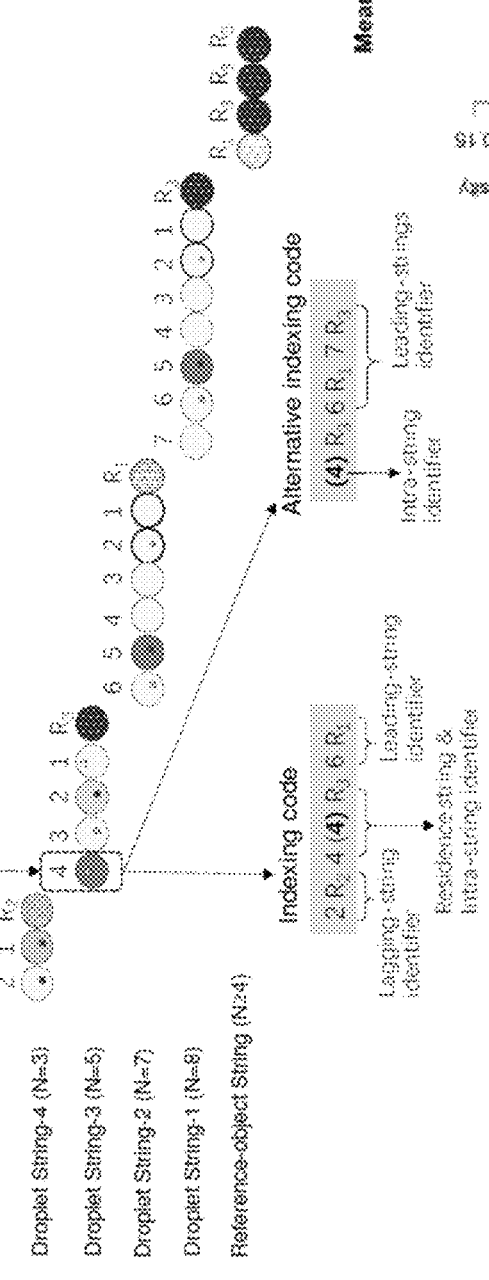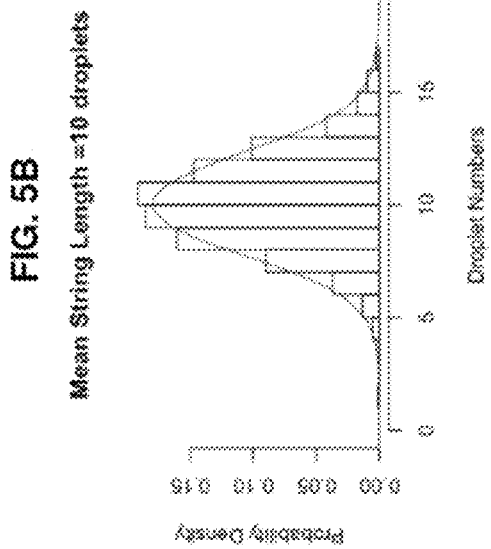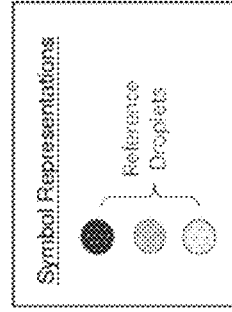
FIG. 5A
FIG. 5B
FIG. 5C

1000 ↘

```
┌─────────────────────────────────────────────────────────────────────────┐
│ INTRODUCE INTO A MICROFLUIDIC DEVICE A PLURALITY OF WATER-IN-OIL        │
│ DROPLETS THAT COMPRISE A PLURALITY OF ASSAY DROPLETS, AS ASSAY          │
│ SAMPLES, AND A PLURALITY OF REFERENCE OBJECTS THAT CONTAIN AT LEAST     │
│ ONE REFERENCE MATERIAL, WITH THE REFERENCE OBJECTS AND ASSAY DROPLETS   │
│ BEING INTERSPERSED IN A SINGLE-STREAM MANNER OR A MULTIPLE-SINGLE-      │
│ STREAMS MANNER IN THE MICROFLUIDIC DEVICE                               │
│                                   1010                                  │
└─────────────────────────────────────────────────────────────────────────┘
                                     ▼
┌─────────────────────────────────────────────────────────────────────────┐
│ COLLECT SIGNAL DATA REPRESENTING SIGNALS FROM INDIVIDUAL REFERENCE      │
│ OBJECTS OF THE PLURALITY OF REFERENCE OBJECTS AND FROM INDIVIDUAL       │
│ ASSAY DROPLETS OF THE PLURALITY OF ASSAY DROPLETS IN THE MICROFLUIDIC   │
│ DEVICE AT TWO OR MORE TIME-POINTS OVER A PERIOD                         │
│                                   1020                                  │
└─────────────────────────────────────────────────────────────────────────┘
                                     ▼
┌─────────────────────────────────────────────────────────────────────────┐
│ PROCESS THE COLLECTED SIGNAL DATA TO IDENTIFY THE INDIVIDUAL REFERENCE  │
│ OBJECTS AND THE INDIVIDUAL ASSAY DROPLETS, AND TO GENERATE A RESPECTIVE │
│ POSITION INDEX FOR EACH OF THE INDIVIDUAL ASSAY DROPLETS BY USING TWO   │
│ OR MORE REFERENCE OBJECTS PROXIMAL TO EACH OF THE INDIVIDUAL ASSAY      │
│ DROPLETS AS A POSITION REFERENCE FOR A GIVEN ASSAY DROPLET OF THE       │
│ ASSAY DROPLETS                                                          │
│                                   1030                                  │
└─────────────────────────────────────────────────────────────────────────┘
                                     ▼
┌─────────────────────────────────────────────────────────────────────────┐
│ ESTABLISH A RESPECTIVE ASSAY-SIGNAL KINETICS FOR EACH OF THE INDIVIDUAL │
│ ASSAY DROPLETS OVER A PREDEFINED PERIOD OF TIME, WITH EACH OF A NUMBER  │
│ OF ASSAY DROPLETS OF THE PLURALITY OF ASSAY DROPLETS WITH A RESPECTIVE  │
│ KINETICS PROPERTY MEETING A PREDEFINED CONDITION BEING ACCORDINGLY      │
│ SELECTED FROM A TOTAL DROPLET POPULATION OF THE PLURALITY OF ASSAY      │
│ DROPLETS                                                                │
│                                   1040                                  │
└─────────────────────────────────────────────────────────────────────────┘
                                     ▼
┌─────────────────────────────────────────────────────────────────────────┐
│ SORT THE SELECTED ASSAY DROPLETS WITH A SORTER DEVICE BY USING THE      │
│ RESPECTIVE POSITION INDEX OF EACH OF THE SELECTED ASSAY DROPLETS AS A   │
│ GUIDE TO GENERATE A SORTER-DEVICE ACTIVATION SIGNAL                     │
│                                   1050                                  │
└─────────────────────────────────────────────────────────────────────────┘
```

```
INTRODUCE INTO A MICROFLUIDIC DEVICE A PLURALITY OF WATER-IN-OIL DROPLETS THAT
COMPRISE A PLURALITY OF ASSAY DROPLETS, AS ASSAY SAMPLES, AND A PLURALITY OF
REFERENCE OBJECTS THAT CONTAIN AT LEAST ONE KIND OF A REFERENCE MATERIAL,
WITH THE REFERENCE OBJECTS AND ASSAY DROPLETS BEING INTERSPERSED IN A SINGLE-
STREAM MANNER OR A MULTIPLE SINGLE-STREAMS MANNER IN THE MICROFLUIDIC DEVICE
                                    1110
```

↓

```
COLLECT SIGNAL DATA REPRESENTING SIGNALS FROM INDIVIDUAL REFERENCE OBJECTS
OF THE PLURALITY OF REFERENCE OBJECTS AND FROM INDIVIDUAL ASSAY DROPLETS OF
THE PLURALITY OF ASSAY DROPLETS IN THE MICROFLUIDIC DEVICE AT TWO OR MORE TIME-
                              POINTS OVER A PERIOD
                                    1120
```

↓

```
PROCESS THE COLLECTED SIGNAL DATA TO IDENTIFY THE INDIVIDUAL REFERENCE
OBJECTS AND THE INDIVIDUAL ASSAY DROPLETS, AND TO GENERATE A RESPECTIVE
POSITION INDEX FOR EACH OF THE INDIVIDUAL ASSAY DROPLETS BY USING TWO OR MORE
PROXIMAL REFERENCE OBJECTS OF THE PLURALITY OF REFERENCE OBJECTS AS A
POSITION REFERENCE, WITH THE RESPECTIVE POSITION INDEX FOR ONE OF THE
INDIVIDUAL ASSAY DROPLETS BEING UNCHANGED OR LARGELY UNCHANGED OVER A FIRST
                           PREDEFINED PERIOD OF TIME
                                    1130
```

↓

```
ESTABLISH RESPECTIVE ASSAY-SIGNAL KINETICS FOR EACH OF THE INDIVIDUAL ASSAY
DROPLETS OVER A SECOND PREDEFINED PERIOD OF TIME, WITH A NUMBER OF THE ASSAY
DROPLETS WITH A PREDEFINED KINETICS PROPERTY BEING ACCORDINGLY IDENTIFIED
FROM A TOTAL DROPLET POPULATION OF THE PLURALITY OF ASSAY DROPLETS
                                    1140
```

FIG. 11

METHOD AND SYSTEM FOR REFERENCE-ASSISTED DROPLET DETECTION, INDEXING AND SORTING FOR ASSAYS AND DIAGNOSTICS

CROSS REFERENCE TO RELATED APPLICATION(S)

The present application is a non-provisional that claims the priority benefit of U.S. Provisional Patent Application Ser. No. 62/500,249, filed on May 2, 2017, content of which is incorporated by reference in its entirety.

TECHNICAL FIELD

The present disclosure is related to assays and diagnostics and, more specifically, to reference-assisted kinetic detection, indexing and sorting of droplets for assays and diagnostics.

BACKGROUND

There are great needs for cutting-edge technologies and systems that can analyze, isolate and quantify individual analytes within a heterogeneous mixture in a high-throughput format. These technologies may find broad applications in biology and chemistry that include pathogen detection, liquid biopsy, affinity reagent screening, rare cell enrichment, metabolite profiling, synthetic biology screening, and drug discovery. Conventional high-throughput systems are commonly based on a microwell plate that is often coupled with robotic liquid handling and flow cytometry systems. An advantage of these traditional systems is the capability to provide precise sample indexing because of the physically fixed well position. Nonetheless, these systems often require expensive instrumentation, large sample and reagent volume, yet with a relatively low throughput. More often than not, users either cannot afford the instruments, or, simply do not have enough starting samples available for the analysis, particularly in cases that involve precious samples such as biopsy, stem cells, and other rare samples.

Microfluidic-based high-throughput technologies are increasingly recognized as an effective alternative to the traditional microwell plate and robotic liquid-handling systems. These microfluidic technologies often partition a bulk sample into many isolated sub-nanoliter compartments in order to increase the effective analyte concentration and simultaneously reduce interferences from irrelevant species present in the same bulk sample. Droplet-based microfluidics represent a fast-growing technology that combines the ability of compartmentalization, the flexibility of fluidic droplet manipulation and the capacity for ultra-high throughput screening. It has additional advantages exemplified by minimal solution evaporation or adsorption of molecules at the device walls. Monodispersed (i.e., homogeneous size) droplets in the range of picoliter to nanoliter volume can be readily generated by a skilled person at kilo-hertz frequencies with sizes precisely controlled by fluid composition, flow rate and droplet-generation device geometry.

Droplet microfluidic devices have been developed for a wide range of applications including directed molecule evolution, pathogen detection, PCRs, single-cell and single-molecule analysis.

There are great needs for microfluidic droplet-based assays that allow precise indexing and tracking of individual assay droplets in a high throughput manner. One clear advantage with the droplet indexing is to enable kinetic or real-time detection of the assay signals, which may effectively identify a potential false-positive or false-negative reaction, and the ones with a user-defined biological or physicochemical property. In the context of drug screening or rare species isolation, there may be further needs to sort the identified droplets for a downstream application. To achieve the similar indexing capacity of a conventional microwell-plate system, there are a few prior designs of droplet-trapping structures or arrays in a microfluidic device. These location-fixed trapping structures may facilitate droplet indexing and detection in a kinetic manner. For instance, one approach used multiple channels with tandem constrictions to trap thousands of droplets, wherein the droplets were subsequently recovered by increasing the flow rate to push the select droplets through the channels. Similarly, another approach exploited the buoyancy of water-in-oil to trap thousands of droplets of sub-nanoliter size in an inverted floating array structure. The droplets in the inverted floating array can be recovered by flipping the device and flushing the trapping wells.

There are examples of stationary one- or two-dimensional droplet arrays. While these fixed-location array designs may enable multi-timepoint kinetic analysis of biological or chemical processes at a low throughput manner similar to that of a conventional plate system, these devices suffer a few critical drawbacks that make their real-world applications rather difficult and limited: 1) the manipulation and sorting of droplets from these types of structures are highly inefficient or virtually impossible; 2) detection synchronization across the droplets is hard to achieve for a large number of assay samples; 3) droplet trapping efficiency is often poor, where the majority of droplets simply flow through the device without being trapped and assayed, leading to significant loss of assay samples that may be precious and hard to procure; and 4) assay throughput is often limited, which is often below 10,000 and thus insufficient for important applications that involve the analysis and screening of a large number of analytes.

On the other hand, there are a few droplet-encoding methods in the context of biochemical assays. For example, there has been proposed for an alternating color-code to identify individual assay droplets with analytes. There is also report on the usage of varied concentrations of magnetic particles to encode assay droplets. Another approach uses a silicon-nanowire based field effect transistor as an electrochemical sensor to probe individual droplets on a grid. Nonetheless, droplet-encoding approaches represented by these prior arts present a few critical pitfalls: (1) the encoding material is commonly co-encapsulated with the assay sample in the same individual droplets, which may adversely affect the accuracy of the assay result and/or the integrity of intra-droplet sample that may be precious and intended to be recovered for further applications; (2) the available combinations of distinguishable codes are usually below 10,000, 1,000 or even 100, which unfortunately precludes any high throughput assay that requires a large amount of droplets in the scale of $10^4$, $10^5$, or higher; (3) complex or expensive instrument setups may be required, and/or (4) in some cases, the underlying detection-decoding process is slow (at the scale of a few tens of milliseconds), which may significantly limit the speed and robustness of the assay.

Thus, new methods and systems are greatly needed, which can precisely control droplet indexing and perform kinetic analysis of indexed droplets in an ultra-high throughput manner. Moreover, at least in the contexts of drug screening and rare cell isolation, there are additional unmet needs to couple the droplet indexing and detection with a downstream sorting module to efficiently recover assay droplets with a pre-defined kinetics property for further analysis or applications.

SUMMARY

The following summary is illustrative only and is not intended to be limiting in any way. That is, the following summary is provided to introduce concepts, highlights, benefits and advantages of the novel and non-obvious techniques described herein. Select implementations are further described below in the detailed description. Thus, the following summary is not intended to identify essential features of the claimed subject matter, nor is it intended for use in determining the scope of the claimed subject matter.

Provided are methods, apparatuses and systems for reference object assisted droplet detection, and sorting. In one aspect, provided are the reference-object types, compositions, and characteristics. Reference object can be a droplet that comprises one or more kinds of reference material. Reference object alternatively can be a solid, semi-solid or soft-solid particle that comprises one or more kinds of reference material, and a support matrix provided by alginate, hydrogel and the likes. The said reference material can be optically detectable molecules represented by fluorescent dyes, or electromagnetically detectable materials represented by magnetic particles. Reference objects may be provided to a microfluidic device through on-demand generation on the device or from an off-the-shelf source.

Provided are also the methods for using reference objects as a dynamic positioning system to index individual assay droplets (i.e., droplets that contain an analyte) which are interspersed with reference objects at a certain ratio. In one aspect, reference objects may punctuate a long "train" of tandem droplets into a plurality of short "droplet strings" of variable lengths (i.e., variable droplet numbers in a stretch). The size of a droplet string will be a random number following certain statistics, and the number combination representing two or more consecutive strings may serve as a string identifier. In another aspect, both the string size and the intra-string position-numbering for a given droplet will remain largely unchanged over time in a spatially confined microfluidic device, although individual droplets are not physically trapped and hence may be mobile with variable gaps in between during an extended period of time. Therefore, one, two or more string identifiers combined with an intra-string identifier may provide a vast amount of diverse codes to effectively index any number of assay droplets, largely avoiding the co-loading of potentially toxic barcode materials into the same assay droplets.

Provided are also systems, individual modules and sub-modules of the said systems, for using reference objects as a dynamic positioning approach to index individual droplets, and for droplet detection and sorting. In one configuration, the components for droplet detection and reference-object sensing can be integrated into a single detection module in a representative case wherein the signals from both the assay droplets and reference objects are physically similar (e.g., both are optical signals). In another configuration, assay droplets and reference objects are detected by two separate sensors, respectively.

BRIEF DESCRIPTION OF THE DRAWINGS

The accompanying drawings are included to provide a further understanding of the present disclosure and are incorporated in and constitute a part of this specification. The drawings illustrate embodiments of the present disclosure and, together with the description, serve to explain the principles of the present disclosure. The drawings may not necessarily be in scale so as to better present certain features of the illustrated subject matter. Like annotation symbols in the various drawings indicate like elements, unless otherwise stated.

FIG. 1A illustrates interspersed assay droplets and reference objects in a segment of a microfluidic device channel. The assay droplets and reference objects can be mixed and arranged in various combinations exemplified by near randomly interspersed pattern and short stretches of tandem droplets or tandem reference objects.

FIG. 1B illustrates interspersed droplets and reference objects in a chamber with one single layer, or two or more layers.

FIG. 2A, FIG. 2B and FIG. 2C illustrate exemplary types of reference objects, which can be liquid droplets containing a reference material, or solid particles containing a reference material.

FIG. 4A and FIG. 4B each illustrates exemplary geometry or shape of a chamber, a cuvette, a cylinder, a vial, or a well that may house one layer, or two or more layers of assay droplets and reference objects in a device, wherein the droplets/reference-objects mixture are configured in a single-stream manner, a parallel single-stream manner, or a multiple-single-streams manner.

FIG. 5A, FIG. 5B and FIG. 5C illustrate the concept of droplet train and droplet string, and that the proximal string-size and the intra-string numbering for a given assay droplet within a droplet string is largely unchanged during an assay period of time. Provided are also exemplary position indexing codes.

FIG. 10 illustrates an example process in accordance with an embodiment of the present disclosure.

FIG. 11 illustrates an example process in accordance with an embodiment of the present disclosure.

DETAILED DESCRIPTION OF THE PREFERRED EMBODIMENTS

Figure 3C:
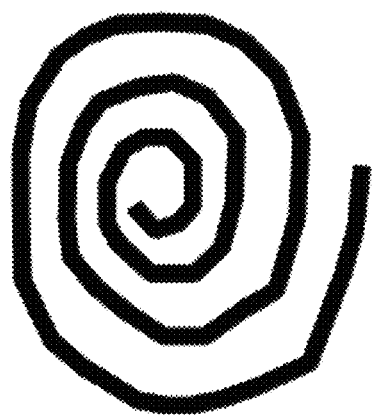
FIG. 3A, FIG. 3B, FIG. 3C and FIG. 3D each illustrates exemplary geometry or shape of a channel or tube that confines the assay droplets and reference objects into plugs in a microfluidic device.
Figure 3D:
Figure 3A:
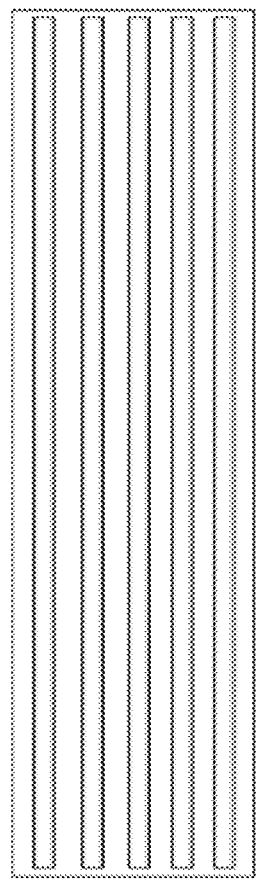
Figure 3B:
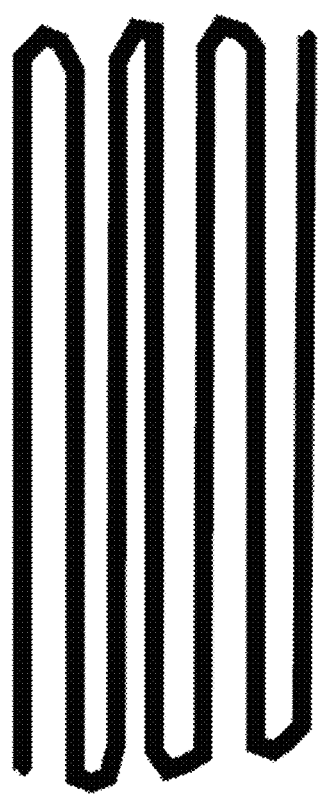

Detailed embodiments of the claimed subject matters are disclosed herein. However, it shall be understood that the disclosed embodiments are merely illustrative of the claimed subject matters which may be embodied in various forms. The present disclosure may, however, be embodied in many different forms and should not be construed as limited to the exemplary embodiments set forth herein. Rather, these exemplary embodiments are provided so that description of the present disclosure is thorough and complete and will fully convey the scope of the present disclosure to those skilled in the art. In the description below, details of well-known features and techniques may be omitted to avoid unnecessarily obscuring the presented embodiments.

Overview

Provided are methods, apparatuses, and platforms to detect, index, track, analyze, and sort a plurality of water-in-oil droplets in a microfluidic device for assays or diagnostics. These may be used in chemical and biological assays for the detection of various analytes (i.e., assay samples) consisting of metabolites, small molecules, proteins, lipids, sugars, nucleic acids, bacteriophages, viruses, cells, and the communications and interactions between and among these analytes. It is expected that a person skilled in the arts may readily produce the said droplets with a syringe- or pressure-pump, a microfluidic chip with a flow-focus or T-junction geometry, and a biocompatible oil such as 3M™ Novec-7500™ oil, all of which are widely accessible in a properly equipped mechanical or biomedical engineering lab or a micro-electro-mechanical systems (MEMS) core facility.

Droplet indexing is achieved by introducing a pool of reference objects into a housing-structure in a microfluidic device or chip for the droplets that contain assay sample and reagent for assay purposes (herein and thereafter "assay droplets"). This indexed droplet assay format may enable the indexing of up to millions or more of droplets without trapping the droplets in fixed locations. Indexing allows for real-time or multi-timepoint detection of a plurality of the same individual droplets, effectively enabling kinetic analysis to recapitulate the dynamic nature of chemical and biological processes in a given droplet. The indexed assay format is also useful for synchronizing reactions from a plurality of droplets. Herein the terms microfluidic device and chip are often used interchangeably, which in general refers to a set of micro-channels etched or molded into a material (glass, silicon, plastic, polymer, or polydimethylsiloxane), where the micro-channels forming the microfluidic chip are connected together in order to achieve the desired features (e.g., mix, pump, sort, control of biochemical environment). It is understood that a person skilled in the art may readily fabricate such a microfluidic device in a properly equipped mechanical or biomedical engineering lab or a micro-electro-mechanical systems (MEMS) core facility.

In some embodiments, reference objects are characterized by one aspect, or two or more aspects of features. In one aspect, a reference object can contain liquid, or non-liquid, or both liquid and non-liquid components. In another aspect, a reference object may contain one type, or two or more types of distinct reference materials.

In some embodiments, a liquid reference object, preferentially exemplified by a droplet, may contain a liquid reference material selected from a group consisting of fluorophore-containing chemicals or molecules or complexes, or colored-dyes, luminescent chemicals, and soluble electrochemical sensors. Preferred liquid reference material is a fluorescent dye or polymer such as FAM (carboxyfluorescein), Calcein AM, Green CMFDA, DRAQ7, Alexa Fluor series of dyes, and DyLight series, and a fluorescent protein such as GFP (Green Fluorescent Protein), EGFP, ZsGreen, mRFP (Red Fluorescent Protein), and mCherry, and a fluorogenic enzyme substrate. It is understood that these liquid reference materials are general reagents or chemicals widely available from a plurality of commercial vendors or may be made in a chemistry lab by a person skilled in the art.

In yet another aspect, a droplet that serves as reference object may contain non-liquid reference material selected from a group consisting of fluorophore-containing particles, quantum dots, colored-beads, magnetic particles, luminescent beads, mass-coded beads, optically-detectable digital beads, and electrochemical sensor beads. In a preferred embodiment, the preferred non-liquid reference materials are fluorescent or magnetic particles. Herein the terms "bead" and "particle" are often used interchangeably, which in general refer to solid objects with a dimension scale ranging from nanometer ("nanoparticle") to micrometer ("microparticle"), which may include but are not limited to a sphere, cylinder, or ellipsoid shape. It is understood that these particulate materials are commonly available from a plurality of commercial vendors or may be made in a chemistry or material-science lab by a person skilled in the art.

In yet another aspect, the reference object can be a solid, semi-solid or soft-solid particle with a support matrix formed by plastic polymers, silicon, glass, inorganic substances, or gel-forming material such as agar, alginate, and hydrogel polymers and pre-polymers. The said reference object further comprises a liquid or non-liquid reference material as described for the said reference droplet. In a preferred embodiment, the preferred reference object is a soft-solid microgel formed by a gel-forming material, wherein the said microgels may deform to fit the inner geometry of a droplet-housing channel or structure in a microfluidic device. It is understood that these gel-forming materials are widely available as consumable reagent or chemicals from a plurality of commercial vendors or may be made in a chemistry or material-science lab by a person skilled in the art.

In yet another aspect, the concentration of reference material in a reference object can be fixed or nearly fixed. For a single assay, there can be one, two or more sets of reference objects that contain the same kind of reference material but at a different concentration level for each individual set. In a preferred embodiment, reference material is a fluorescent dye or polymer which is provided in a reference droplet at one, two, three and up to a few tens of distinguishable concentration levels, each of which is within the dynamic resolution range of an optical detector such as a photomultiplier tube (PMT), in a way similar to the dye-coated Luminex™ beads. In yet another preferred embodiment, one, two, three and up to ten distinguishable concentration levels can be specified for a reference material comprising magnetic particles. In a prior art, it is reported that at least ten different magnetic barcoded particle concentrations can be distinguished by a magnetic sensor based on a giant magnetic resistor (GMR).

In yet another aspect, the reference material is preferentially stable over an extended period of time, and detectable within the dynamic detection range of a signal detector. Preferred reference material is a fluorescent dye or bead or polymer, or a magnetic particle, which is stable over an extended period of time in a properly stored condition. Herein the term "stable" primarily refers to biophysical and chemical stability.

The reference material provided herein in general refers to a single component of, or a complex with one, two or more components that are derived from chemicals, dyes, molecules, proteins, barcodes, labels, tags, beads, microspheres and nanoparticles. The bead provided herein in general refers to solid or semi-solid particles selected from a group consisting of organic and inorganic microbeads, polystyrene or plastic or glass beads, microspheres, silicon beads, nanoparticles, quantum dots, magnetic or paramagnetic beads, agarose gels, alginate gels, and hydrogels, which have a diameter range from 1 nm to 100 µm, preferentially from 10 nm to 10 µm, and more preferentially from 50 nm to 6 µm. Preferred is fluorophore-containing particles that are exemplified by a streptavidin-labelled Alexa Fluor 488 dye.

The barcode provided herein in general refers to a fluorescence barcode, a colored-coded barcode, an optically-detectable digital barcode, and a magnetic barcode. Preferred is a fluorescence-labelled barcode exemplified by the Luminex barcode beads and NanoString's digital color-coded barcodes. Under many circumstances, barcodes are also interchangeably referred to as tags.

The concentration of a reference material provided herein may be used in a reference object at a range from 1 aM (attomolar) to 20 M (molar), preferentially from 10 fM (femtomolar) to 2 M, more preferentially from 10 pM (picomolar) to 500 micromolar (µM) and even more preferentially from 1000 pM to 100 µM.

In some embodiments, in addition to comprising an analyte, the assay droplet may comprise a low but quantitatively detectable level of reference material in order to facilitate the identification and counting of the said assay droplets.

In some embodiments, assay droplets and reference objects can be of a similar homogeneous size ("monodisperse") or heterogeneous sizes ("polydispersed"), which may range from 0.0001 picoliter to 100 nanoliter, preferentially from 0.1 picoliter to 10 nanoliter, and more preferentially from 1 picoliter to 3 nanoliter, and even more preferentially from 30 picoliter to 1 nanoliter.

In some embodiments, assay droplets are mixed with reference objects at a droplet/reference-object ratio ranging from 100,000:1 to 1:5, preferentially from 1000:1 to 1:1, and more preferentially from 50:1 to 5:1. Assay droplets and reference objects can be generated on-demand and introduced as a mixture into the droplet-housing structure of a microfluidic device through a droplet generator and a mixer unit. In alternative embodiments, reference objects can be pre-made and stored at a reservoir before being injected into the device. Preferentially, various standard formats of reference objects can be made off device and used as routine off-the-shelf reagents for a plurality of assays.

In some embodiments, the interspersed droplets and reference objects can be incubated on a microfluidic device, in the presence of one or more environmental control units selected from a temperature control unit (with a preferred temperature range of about 4° C.–98° C.), an oxygen control unit (with a preferred $O_2$ level of about 0.01%-30%), a carbon dioxide control unit (with a preferred $CO_2$ level of about 0.1%-20%), and a humidity control unit (with a preferred humidity level of about 50% to 99%).

In some embodiments, among the mixture of droplets and reference objects housed in a microfluidic device, two or more reference objects can be juxtaposed to each other in a tandem manner along the flow direction as a "reference-object string" in a beginning, middle or tail section of a droplet-housing structure. Within a given reference-object string, replicate or distinct reference objects, in terms of reference-material composition and concentration, can be included. Each continuous segment of assay droplets plus a flanking reference object can be considered as a "droplet string", and there exist a plurality of such strings with variable droplet numbers in a given channel of a device.

In some embodiments, the assay droplets and reference objects can be incubated on a device with a droplet-housing structure that is exemplified by a straight channel, a curved channel, a spiral tube, and a combination of two or more types of said channels or tubes with various geometries.

In some embodiments, the assay droplets on a device can be detected during the incubation period, by using a proper signal detector. Exemplary detectors are an optical detector for detecting optical signals such as fluorescence, light-absorbance, luminescence, and scattering light signal. Alternative exemplary detector is a silicon-nanowire based field effect transistor (SiNW FET) for detecting electrochemical signals. Preferred is an optical detection module comprising a photon sensor and a signal amplification unit, which can be selected from a group consisting of a charge-coupled device (CCD) camera, a complementary metal-oxide semiconductor (CMOS) sensor, a photomultiplier, and an avalanche photodiode (APD). The detection module can be connected to a signal acquisition and processing board, which can be integrated with a computer equipped with process-control and user interface software.

In alternative embodiments, the reference objects and assay droplets may be detected and enumerated based on signal data collected from a common detector that detects both signals representing assay readout and reference material, or from two detectors that detect signals representing assay readout and reference material, respectively. Exemplary detectors are an optical detector for detecting optical reference materials such as fluorescent dyes, a magnetic detector such as a giant magnetoresistance (GMR) sensor for detecting magnetic particles, and a field effect transistor for detecting electrochemical materials. In some embodiments, reference materials are detected in a qualitative or quantitative manner by using a said detector.

In some embodiments, the interspersed assay droplets and reference objects may run like a "droplet train" through a signal detection area two or more times or repeatedly via a flow-returning mechanism (e.g., a flow loop or a dual-direction pump). Herein the term "droplet train" refers to a single stream of droplets that has a reference-object string at the beginning of the stream along the flow direction, followed by two, three or more droplet-strings punctuated with isolated single reference objects or a tandem stretch of multiple reference objects (i.e., a reference-object string).

In some embodiments, among the interspersed mixture of assay droplets and reference objects on a device, a given assay droplet can be coded by a position index code. In one aspect, reference objects are provided to randomly punctuate assay droplets into numerous short "droplet strings" of variable population sizes, which usually follow a normal distribution when the total number of droplet strings approaches 50,100, or higher, in part dictated by the Large Number law. The number combination representing the respective population of two or more tandem strings may effectively serve as a digital identifier for the said strings. In another aspect, the ordered intra-string index and the string population containing a given droplet will remain largely unchanged in a device that confines the droplet/reference-object mixture into a single stream or multiple parallel streams, even with non-stationary individual droplets over a period of time. Therefore, the identifiers for two or more consecutive strings combined with an intra-string identifier for a given assay droplet may provide a large number of unique codes to effectively index any assay droplet, leaving the assay droplets largely free of potentially toxic barcode materials. In some embodiments, the terms "detector" and "sensor" are used interchangeably.

In some embodiments, an assay droplet can be indexed by the combination of digital identifiers representing: (1) the "residence string" that contains the said droplet to be indexed, (2) the intra-string position numbering of the said droplet, and (3) at least one leading droplet string that is immediately ahead of the residence string along the flow direction. For one non-limiting example, given about 10% reference objects of two different populations (each with a distinct reference-material concentration), which are randomly interspersed with the bulk assay droplets in a single-stream (e.g., single-line) manner, and also given three leading strings to assist the position indexing, there will be up to about 220,000 diverse codes to index the assay droplets. For another non-limiting example, given about 5% reference objects with four distinct reference-material concentration levels respectively, and using four leading strings to assist the position indexing, there will be up to about 302 million diverse codes to index the assay droplets. Such a large number of unique codes is more than adequate for the majority, if not all, of known ultra-high throughput assays.

In alternative embodiments, an assay droplet can be indexed by the combination of digital identifiers representing: (1) the residence string that contains the said droplet to be indexed, (2) the intra-string position numbering of the said droplet, (3) at least one leading string immediately ahead of the residence string along the flow direction, and (4) at least one lagging string immediately behind. For example, given about 5% reference objects of three distinct reference-material-concentration levels, which are randomly interspersed in the bulk assay droplets in a single-stream manner, and using two leading and one lagging string(s) to assist the position indexing, there will be as many as about 1.6 million diverse codes to index the assay droplets.

In some embodiments, data acquisition from the signal detection module and/or the counting sensor are performed by a signal acquisition and processing board at two, or three or more time-points or in a real-time fashion to provide serial data points that are used to establish signal kinetics for individual droplets.

In some embodiments, the acquired data are processed in a real-time or near real-time mode by a signal acquisition and processing board to provide position indexing and kinetics modeling for the assay droplets. Based on the kinetics property, a portion or all of the droplets with a customer-defined kinetic property can be identified and selected with the guidance of their respective position index, based on which the said signal processing board can send a digital trigger to sequentially activate a downstream sorting module.

In some embodiments, the sorting module is based on a dielectrophoretic (DEP), an acoustic, a microvalve, a piezoelectric, a dynamic stream deflection, or an electrical capacitance mechanism. Preferred is a DEP- or acoustic-based sorting module. The said sorting module may serve to collect selected droplets with the guidance of their respective position indexing code. The term "sorting" is often used interchangeably with "retrieving" or "recovering" in an arranged or controlled manner in the context of isolating selected targets with a certain desired property.

In some embodiments, products of manufacture as provided herein are synchronized or integrated with digital communication and computer or mobile device applications. In some embodiments, products of manufacture as provided herein are used in assays and diagnostics for detecting and quantifying a chemical, biological, environmental, water, forensic or food analyte, or a single molecule or a single cell in a single-plex, duplex-, or multi-plex assay format.

In alternative embodiments, wherein the cell is a human cell, an animal cell, a fused hybrid cell, a hybridoma cell, a fungal cell, a yeast cell, a bacterium, a mycoplasma, a virus, an engineered cell, a CRISPR-cas9 edited cell, a Chimeric Antigen Receptor T cell (CAR-T cell), a virally infected cell, a transfected cell, or a drug-treated cell. Optionally a heterogeneous cell pool can be partitioned and encapsulated into individual droplets and characterized, imaged, manipulated and sorted at a single-cell level, and optionally a droplet can contain a single cell, or two or more cells of the same type or different types at various ratios.

Illustrative Embodiments

We show that reference objects with a specified material type and concentration can be utilized to establish a position-referencing system in a droplet-based assay or diagnostics. As exemplary embodiments, FIG. 1 illustrates interspersed reference objects within a bulk of assay droplets in a droplet-housing structure exemplified by a channel and a chamber. Reference objects are preferentially included at a percentage representing 1% to 20% of the total droplets and reference objects population, and preferentially display as distinct, stable and quantifiable signals that are readily detectable during an extended period of assay time using a proper signal detector. The average number of assay droplets between neighboring reference objects can be specified within a certain range with a normal variation by changing the droplet/reference ratio and carrier oil flow rate. As such, these reference objects may randomly punctuate a single-line droplet population into droplet strings. The size of neighboring strings and the intra-string position of a given assay droplet may collectively constitute a unique position code used for indexing the said assay droplet to allow the kinetic or near real-time analysis of the presumably heterogeneous and dynamic assay signals.

In FIG. 2A, a reference object is represented by a droplet that contains soluble material exemplified by fluorescent molecules or complexes, or colored dyes. Alternatively, the reference material in the said reference droplet can be fluorescent- or color-coded particles, or magnetic particles, or electrochemical sensors. The reference material is preferentially of a specific concentration or one of the serial concentration levels, is stable over the assay period, and is readily detectable using a signal detector. In alternative embodiments (FIG. 2B), reference object is a particle that comprises a reference material and a solid matrix formed by plastic polymers such as polystyrene, silicon, glass, organic or inorganic substances, and gel-forming material exemplified by agar, alginate, and hydrogel polymers and pre-polymers. In alternative embodiments (FIG. 2C), an assay droplet may comprise, besides an analyte, a low yet distinguishable level of reference material to facilitate the identification and/or counting of the said assay droplet.

A droplet housing structure within a microfluidic device (often a microfluidic cartridge or chip made of plastic or glass) can be designed by using a Computer Aided Design (CAD) tool. Exemplary channel configurations are shown in FIG. 3, which can be a single channel or a plurality of parallel single-channels, which may have a straight, curved, serpentine, or spiral shape, or any other regular and irregular curvature feature. The channel structure will preferentially house a single stream of the droplet/reference-object mixture. Alternatively, multiple single-streams of a droplet/reference-object mixture can be housed and confined in a two- or three-dimensional chamber. Exemplary chamber configurations are shown in FIG. 4. The chamber can be a two-dimensional "flat box" with various regular and irregular shapes, exemplified by a rectangle, a semicircle, a triangle, and a trapezoid, which are capable of housing a single-layer of the droplet/reference-object mixture within a 2D housing area. Alternatively, the chamber can be a three-dimensional container with various regular and irregular shape, capable of housing multiple layers of the droplet/reference-object mixture within a 3D housing volume. Exemplary microfluidic device geometries may be exaggerated or not drawn to scale, and the inlet and outlet for the device are not always shown in the rendering for visualization purposes.

In some embodiments (FIG. 5A), the assay droplets and reference objects are arranged as a single stream in a channel of a microfluidic device (i.e., like a "droplet train"). The reference objects and assay droplets can be detected using a signal detector that detect both the stable reference-object signals and the heterogeneous assay signals. The reference objects and assay droplets may also be enumerated based on the collected signal data and registered in the positioning system. Each continuous segment of assay droplets is "tagged" by one, two or more adjacent reference objects. Together, the tagged droplet segment plus one leading reference-object can be considered a distinct "droplet string", and there exist a plurality of distinct strings of various sizes among a droplet train in the channel of the device (FIG. 5B). By controlling the relative ratio of introduced assay droplets versus reference objects, the size (i.e., the number of assay droplets and reference objects) of a string in a given assay will follow a normal distribution with a distinct mean and a standard deviation (FIG. 5C). In a channel, tandem units of strings can be identified based on the unique combination of random string sizes. At different time points during the incubation and detection, there could be position shift for a given droplet. However, the said droplet's spatial position numbering within its residence string will remain unchanged or largely unchanged. Rare events such as a random gap, an air bubble, a droplet-droplet fusion, and a droplet splitting, may occur to a droplet string. However, the resulting error of position index will be largely limited to that string, with little effect on adjacent strings, and even less on farther strings. Thus, the usage of droplet strings may effectively reduce tracking errors and facilitate the precise indexing of individual assay droplets within the dynamic reference position map. Exemplary position index codes are shown (FIG. 5C), either referenced by a few leading-strings immediately ahead of the residence string of a given assay droplet, or by using a few leading-plus lagging-strings.

Figure 6:
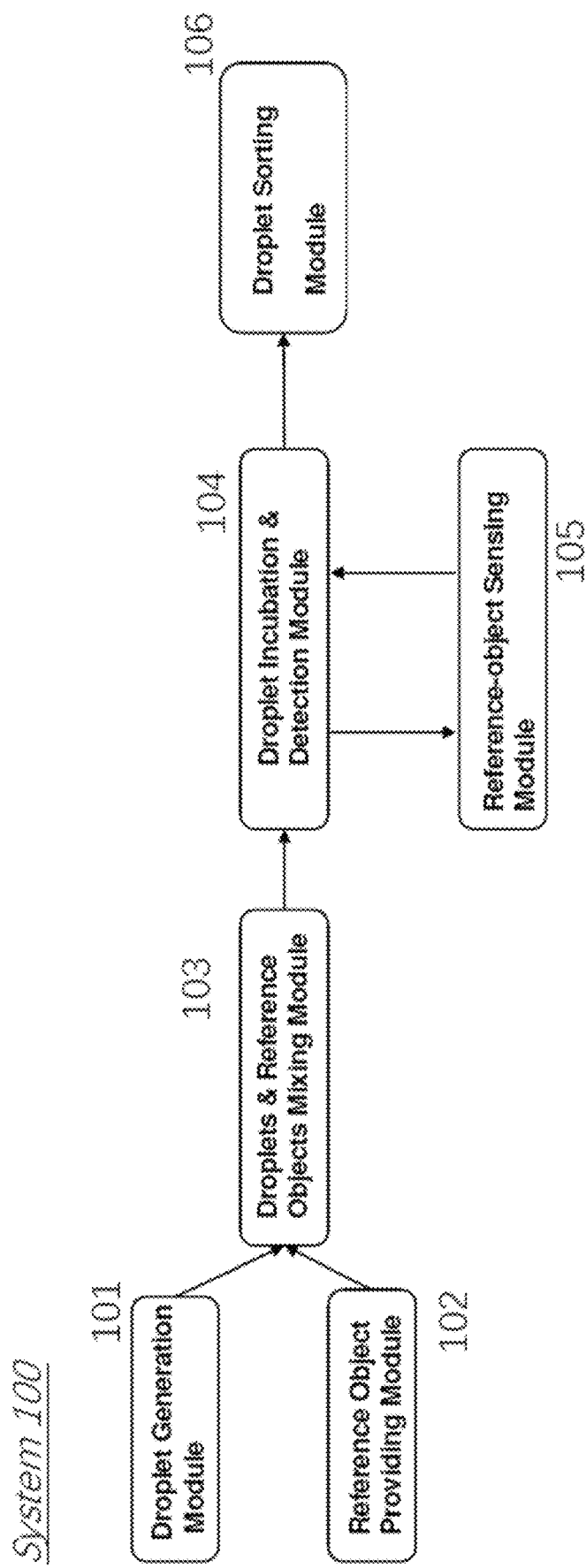
FIG. 6 illustrates an exemplary system for reference assisted droplet indexing, incubation, detection, and sorting.
Figure 7:
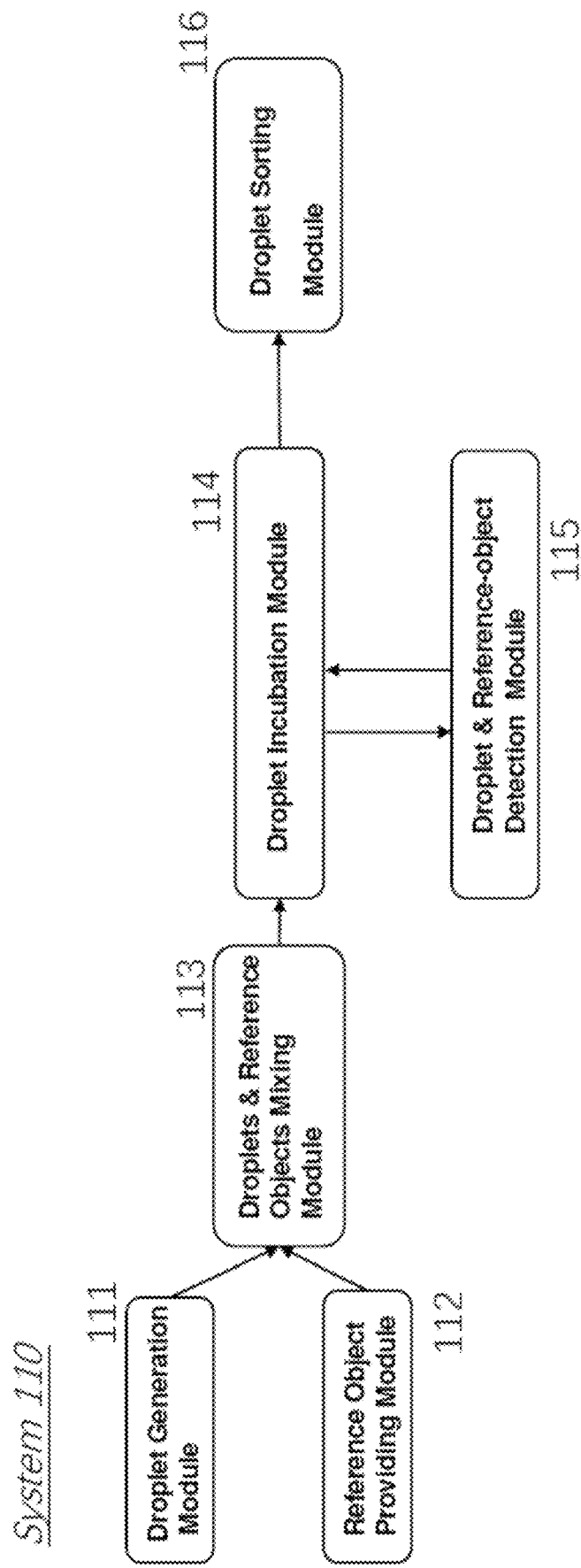
FIG. 7 illustrates an alternative exemplary system for reference assisted droplet indexing, incubation, detection, and sorting.

In some embodiments (FIG. 6), an exemplary reference-assisted droplet assay system 100 and workflow outline for the droplet indexing, detection, and sorting is shown, which may consist of an assay-droplet generation module 101, a parallel reference-droplet providing module 102, a mixer module 103, a droplet incubation and detection module 104, and a parallel reference-object sensing module 105, and a droplet sorting module 106. In an alternative exemplary system 110 (FIG. 7), the sub-modules for droplet detection and reference-object sensing are integrated into a single module. These exemplary system and workflow outlines are by no means limiting, which may comprise additional features that are not shown in the rendering for simple visualization purposes.

Figure 8:
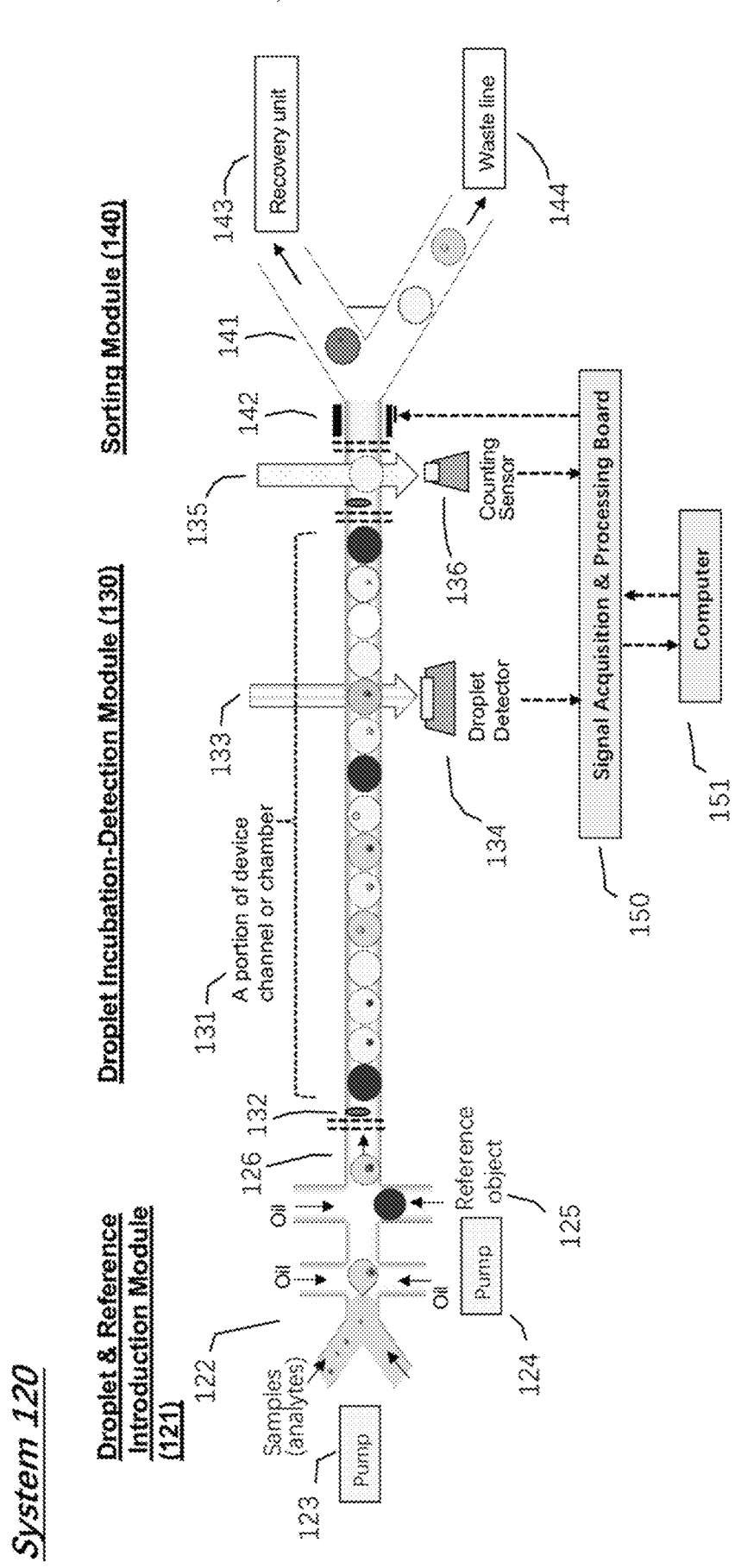
FIG. 8 illustrates an exemplary system showing detailed major modules for reference assisted droplet indexing, detection, and sorting.

In some embodiments, a detailed exemplary reference-assisted droplet assay system 120 is illustrated (FIG. 8), which comprises a droplet and reference-object introduction module 121, a droplet incubation-detection module 130, and a droplet sorting module 150. The said module 121 comprises flow-driving pumps 123 and 124 for introducing samples (analytes), reagents, and reference objects 125, through a droplet generation chip 122. The said module 130 comprises droplet incubation structure (i.e., a portion of a device channel of chamber 131), controllable valves 132, a signal detection energy source 133 (e.g., laser or LED light source), a droplet detector 134, an optional reference-object detection energy source 135, and a reference-object counting sensor 136. The said sorting module 140 comprises a sorting structure 141, a sorting actuator unit 142, a downstream recovery unit such as carousel 143, and a waste line unit 144. The said modules for droplet incubation-detection and sorting are integrated with a signal acquisition and processing board 150, and a computer 151. Arrows indicate the flow direction. Herein the exemplary system 120 is by no means limiting, which may comprise additional features that are not shown in the rendering for simple visualization purpose.

In some embodiments, the signal processing board can be based on a microcontroller or microprocessor (MCU), a field-programmable gate array (FPGA), and/or an application specific integrated circuit (ASIC). It is understood that these signal processing boards are commonly available from a plurality of commercial vendors and can be programmed by a person skilled in the art for the need of a specific application.

Figure 9A:
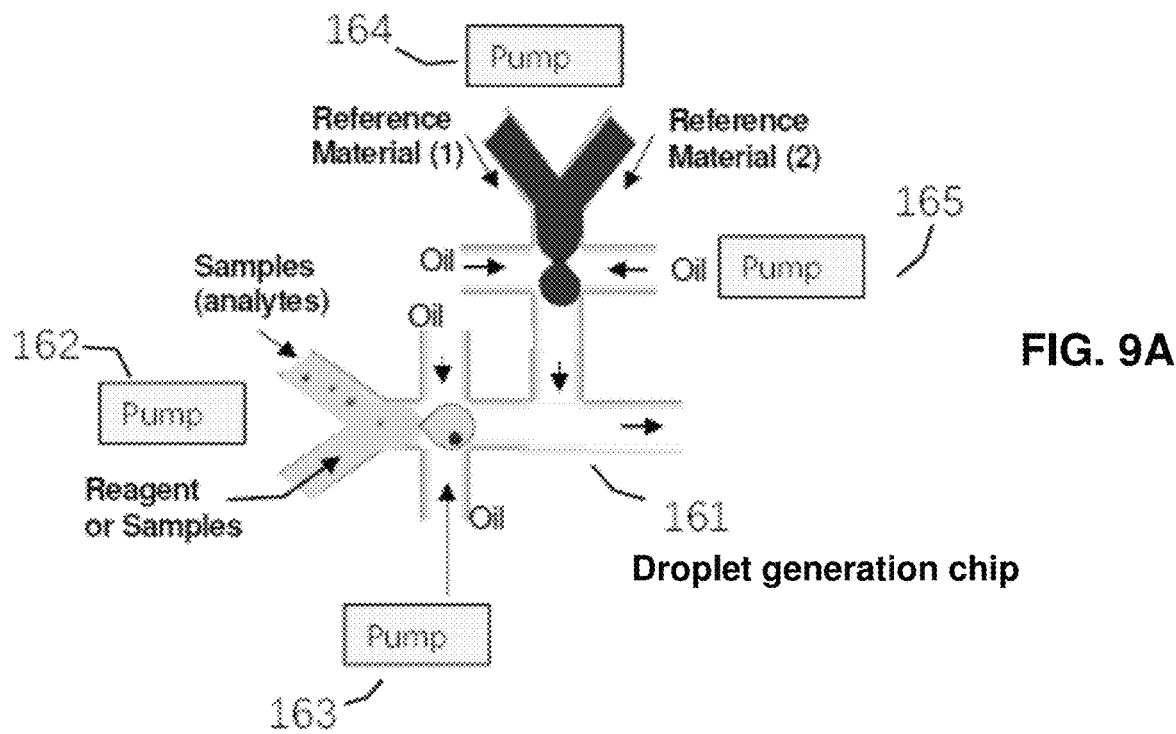
FIG. 9A and FIG. 9B illustrate exemplary modules for providing assay droplets and reference objects into a microfluidic device.
Figure 9B:
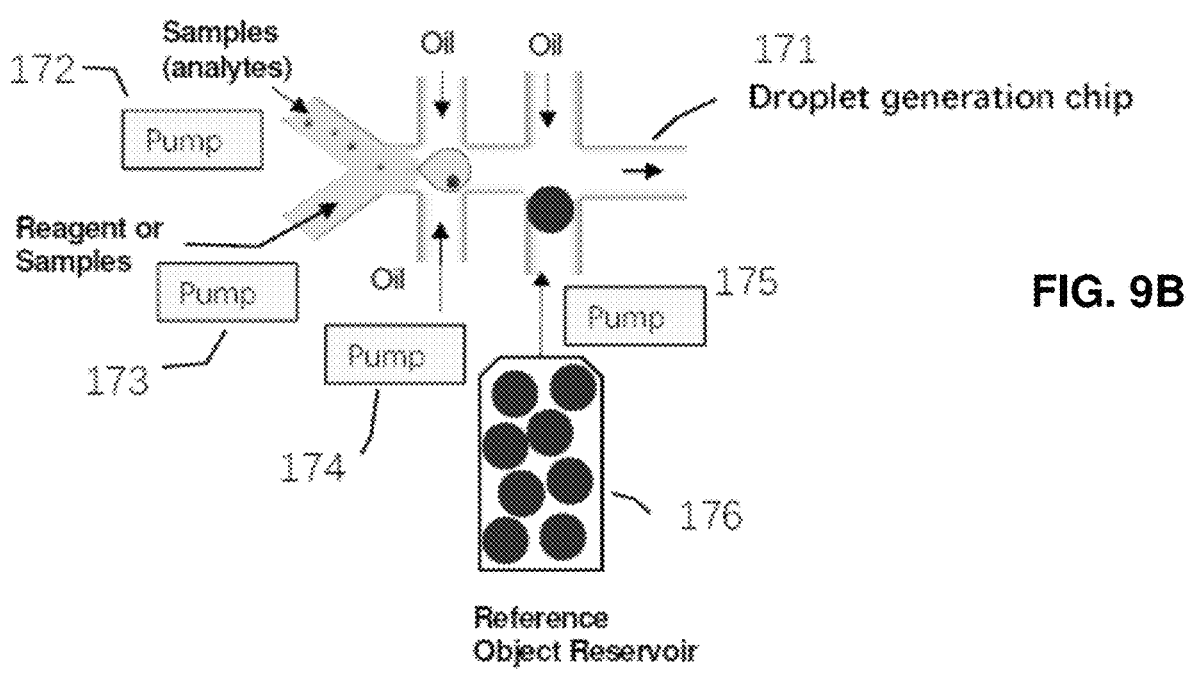

In some embodiments (FIG. 9A), reference objects can be generated on demand using an exemplary generator module 160 and mixed together with droplets on a microfluidic chip 161. In alternative embodiments (FIG. 9B), reference objects can be introduced using alternative device module 170 as a standard off-the-shelf reagent that are pre-made and stored in a reservoir 174. It is understood that a person skilled in the art can readily make such reference objects (droplet- or particle-based) in a chemistry or material-science lab or core facility.

In some embodiments, products of manufacture can provide indexing of a plurality of droplets, which is needed for real-time monitoring over an extended period of time. For example, it can be used for many applications (particularly in a high throughput format) such as single-cell analysis, single-molecule analysis, enzymatic analysis, genetic sequencing, biochemical profiling, metabolism profiling, cell-cell communication analysis, cell culture, pathogen detection, synthetic biology screening, and drug discovery.

In alternative embodiments, a reference-assisted droplet assay system as provided herein can be integrated with various functions for further manipulating droplets such as droplet-droplet fusion, droplet splitting, or droplet breakage to recover the cell or molecule content inside droplet for further culturing or analysis.

In alternative embodiments, a reference-assisted droplet assay system as provided herein can be used for screening and analysis as a diagnostic or research product, a point-of-care technology or product, when combined with CMOS, CCD, or cell phone-based imaging systems. Laser, LED (light emitting diode), UV lamp or LCD panels can be used as an excitation light source.

In alternative embodiments of a reference-assisted droplet assay system as provided herein, the length, size, shape and spacing of the droplet housing structure can be varied as exemplified in FIG. 3 and FIG. 4.

In alternative embodiments of a reference-assisted droplet assay system as provided herein, the efficiency of single-cell encapsulation or two-cell co-encapsulation can be improved by using an inertial flow design, a hydrodynamic flow design, or an active sorting unit before the incubation step.

In alternative embodiments of a reference-assisted droplet assay system as provided herein, the droplet can be retrieved by using a dielectrophoretic (DEP) sorting unit, an acoustic sorting unit, a microvalve-based sorting unit, a piezoelectric sorting unit, or a dynamic stream deflection sorting unit, or an electrical capacitance-based sorting unit. Preferred is a DEP or acoustic based sorting unit that can be activated by an upstream trigger signal.

Alternative exemplary embodiments will be further described with reference to the following examples; however, it is to be understood that these exemplary embodiments are not limited to such examples.

EXAMPLES

Example 1: Kinetic Detection of Cell Secreted Factors

Cells and detection reagents for the cell-secreted factors (e.g., IL-2, IL-12, TNFα, IFNγ, immunoglobulin, and/or IL-4) can be co-encapsulated as assay droplets, which are then co-introduced with reference objects into a microfluidic device and subject to analysis using the exemplified methods and systems. The detection reagents can be a fluorescent-labelled secondary detection antibody plus a target-specific primary antibody conjugated to a microbead. Time-dependent secretion and enrichment kinetics of the analyte can be measured based on the fluorescence focus-intensity changes on the detection bead. Droplets with desired secretion kinetics can be identified and selected. The droplets can be indexed and sorted with the assistance of reference-objects as a position reference system that contain a spectrally distinct and detectable fluorescent dye (e.g., dextran labelled with FITC dye)

Example 2: Real-Time Digital PCR and Real-Time PCR

Polymerase Chain Reaction (PCR) is an enzymatic thermocycling reaction that is commonly used to amplified nucleic acids in biomedical researches and diagnostic assays. DNA polymerase enzymes, dNTPs, oligo-DNA primers, and fluorescent detection probes can be co-encapsulated in assay droplets, which are then co-introduced with reference objects into a microfluidic device for a PCR. The kinetic monitoring of thermocycle accumulation of fluorescent PCR products is a key feature of real-time PCRs. On the other hand, digital droplet PCR (ddPCR) has been developed in part on the basis of partitioning nucleic acid templates adequately to achieve single-molecule per droplet. Our disclosed methods and systems may allow the real-time analysis of ddPCRs by precisely indexing each individual assay droplet that contains zero or one nucleic acid template, thus effectively enabling further reduction of false positive or false negative amplification signals.

Example 3: Kinetic Enzymatic Activity Assay

Enzymes, assay reagents and fluorogenic substrates can be co-encapsulated in assay droplets which are then co-introduced with reference objects as an interspersed mixture into a microfluidic device, and further subjected to indexed real-time analysis to establish enzymatic reaction kinetics and derivation of important biochemical properties, such as substrate specificity and binding properties (e.g., $K_d$, $K_{off}$ and $K_{on}$). References object can be generated on-device or off-the-device in a premade stock.

Example 4: Kinetic Analysis of Cell-Cell Interaction and Cell-Cell Fusion

Single cells of different tissue types or subtypes can be co-encapsulated into assay droplets and introduced into an exemplary microfluidic device together with reference objects.

a) To monitor cell-cell communication and/or direct interaction at the single-cell level. Two different types of cells (e.g., an engineered CAR-T or TCR-T cell and a target cancer cell) can be co-encapsulated into assay droplets, which are then inter-mixed with reference droplets containing a reference fluorescence dye, by using the disclosed method and system. Fluorogenic reagents or cell-based reporter (fluorescent or chemiluminescent) can be used to assess whether the T cell can physically interact with and be activated by the co-encapsulated target cancer cell.

b) In some embodiments, a kinetic cell-cell interaction assay can be used to screen for antibodies that exert a specified function (e.g., activate or block a cell surface receptor of a target cell). For example, to detect target cells effected by primary B cells or hybridomas, these antibody-secreting B or hybridoma cells can be compartmentalized as individual single cells in droplets. In a separate set of droplets, target cells and detection reagents can be encapsulated and then the two sets of droplets are fused pairwise to achieve 1-to-1 cell pairing in a resultant assay droplet (i.e., only one antibody-expressing cell and one target cell).

Example 5: Kinetic Screening for Receptor-Ligand Interaction and Receptor-Binding Therapeutics To monitor a receptor-ligand interaction (e.g., a receptor vs its polypeptide ligand) using the disclosed methods and systems, the two proteins can be co-encapsulated into assay droplets, which are then introduced into a device together with reference objects and subjected to the monitoring by means of fluorescence detection (e.g., conventional laser fluorescence detection, Fluorescent Resonance Energy Transfer (FRET), fluorescent life-time imaging, and fluorescence polarization).

To screen for a receptor-binding molecule as a therapeutic lead, a target protein and detection reagents can be co-encapsulated with individual molecules selected from a library (e.g., small molecules, DNAs, peptides, antibodies or aptamers) in respective droplets. Inhibitory or activational effect can be monitored using conventional laser fluorescence detection, FRET, fluorescence life-time imaging, or fluorescence polarization.

Example 6: Kinetics Based In Vitro Molecule Evolution, Selection and Screening

A disclosed exemplary method and system can be used for in vitro molecule evolution, selection and screening. An aptamer (or DNAs, RNAs or expression viruses or bacteriophages) library can be compartmentalized individually with a target molecule (e.g., a protein, a metabolite, a complex lipid or sugar) within a plurality of assay droplets. Then the assay droplets and reference objects are introduced as a randomly interspersed mixture into an exemplary microfluidic device for the kinetic detection of target-aptamer interactions which may result in a fluorescence signal, for example, by triggering a FRET. Position indices of the assay droplets with desired signal property can be identified to allow subsequent recovery the aptamer clones for further functional validation and/or a next round of molecular evolution process.

Example 7: Kinetic Screening of Genome-Edited Cells

A disclosed exemplary method and system can be used for the screening of single cells that have been subjected to a CRISPR-cas9 mediated genome editing. Exemplary cells subject to engineering are T cells, B cells, dendritic cells, Natural Killer cells, stem cells, progenitor cells, beta cells, muscle cells, neuron cells, yeast cells, and bacteria. Edited (i.e., engineered) cells can be compartmentalized within sub-nanoliter assay droplets and introduced into a device together with reference objects containing at least one distinct reference material (e.g., Texas Red-conjugated dextran), for subsequent measurement of a readout signal that reflect the cell function or phenotypes. Exemplary readout signal can be a GFP-reporter, a luminescent reporter, a fluorogenic substrate, or a fluorescent labelled detection bead, which is spectrally separable from the reference material. Desired assay droplets can be identified based on the respective readout-signal kinetics, and sorted for further culture, downstream molecular and genetic analysis, or other applications.

Illustrative Processes

FIG. 10 illustrates an example process 1000 in accordance with an implementation of the present disclosure. Process 1000 may represent an aspect of implementing the proposed concepts and schemes such as one or more of the various schemes, concepts and examples described above with respect to FIG. 1A-FIG. 9B. More specifically, process 1000 may represent an aspect of the proposed concepts and schemes pertaining to reference-assisted kinetic detection, indexing and sorting of droplets for assays and diagnostics. Process 1000 may include one or more operations, actions, or functions as illustrated by one or more of blocks 1010, 1020, 1030, 1040 and 1050. Although illustrated as discrete blocks, various blocks of process 1000 may be divided into additional blocks, combined into fewer blocks, or eliminated, depending on the desired implementation. Moreover, the blocks of process 1000 may be executed in the order shown in FIG. 10 or, alternatively in a different order. Furthermore, the blocks of process 1000 may be executed iteratively. Process 1000 may begin at block 1010.

At 1010, process 1000 may involve introducing into a microfluidic device a plurality of water-in-oil droplets that include a plurality of assay droplets, as assay samples, and a plurality of reference objects that contain at least one reference material. The reference objects and assay droplets may be interspersed in a single-stream manner or a multiple-single-streams manner in the microfluidic device. Process 1000 may proceed from 1010 to 1020.

At 1020, process 1000 may involve collecting signal data representing signals from individual reference objects of the plurality of reference objects and from individual assay droplets of the plurality of assay droplets in the microfluidic device at two or more time-points over a period. Process 1000 may proceed from 1020 to 1030.

At 1030, process 1000 may involve processing the collected signal data to identify the individual reference objects and the individual assay droplets, and to generate a respective position index for each of the individual assay droplets by using two or more reference objects proximal to each of the individual assay droplets as a position reference for a given assay droplet of the assay droplets. Process 1000 may proceed from 1030 to 1040.

At 1040, process 1000 may involve establishing a respective assay-signal kinetics for each of the individual assay droplets over a predefined period of time. Each of a number of assay droplets of the plurality of assay droplets with a respective kinetics property meeting a predefined condition may be accordingly selected from a total droplet population of the plurality of assay droplets. Process 1000 may proceed from 1040 to 1050.

At 1050, process 1000 may involve sorting the selected assay droplets with a sorter device by using the respective position index of each of the selected assay droplets as a guide to generate a sorter-device activation signal.

In some embodiments, the assay droplets may contain a biological sample, a chemical sample, a food sample, a water sample, a forensic sample, an environmental sample, a derivative of one or more thereof, or a mixture of one or more thereof.

In some embodiments, the assay droplets may contain one or more kinds of light-emitting or light-absorbing substrates or reagents, which allow detection of optical signals as an assay readout.

In some embodiments, the assay droplets may contain one or more kinds of inducible or pre-provided fluorophore-containing reporter molecules, which allow detection of fluorescent signals as an assay readout.

In some embodiments, the reference objects may include water-in-oil droplets with a similar shape and size as that of the assay droplets in the microfluidic device. The size of one of the reference objects may be similar to that of one of the assay droplets with a deviation of less than 60%.

In some embodiments, the reference objects may include a solid or liquid-solid-mixed object with a similar shape and size as that of the assay droplets in the microfluidic device. The size of one of the reference objects may be similar to that of one of the assay droplets with a deviation of less than 60%.

In some embodiments, the reference material in the reference objects may include one or more kinds of fluorophore-containing materials selected from a group comprising chemicals, molecules, dyes, proteins, polymers, particles, barcodes and complexes.

In some embodiments, the reference material in the reference objects may include one or more kinds of color-coded materials selected from a group comprising chemicals, dyes, particles, polymers, and barcodes.

In some embodiments, the reference material in at least one of the reference objects may include magnetic or para-magnetic particles. The magnetic particles may have a size ranging from about 1 nm to about 30 μm.

In some embodiments, the solid or liquid-solid-mixed reference object may include a support matrix of plastic polymers, organic polymers, glass, silicon, or gel-forming polymers or pre-polymers.

In some embodiments, the solid or liquid-solid-mixed reference object may include a soft-solid support matrix of a gel forming substrate comprising alginate, or hydrogel polymers or pre-polymers.

In some embodiments, the reference material in the reference objects may be of a serial level of concentrations. The serial level of concentrations may range from 1 aM (attomolar) to 10 M (molar).

In some embodiments, a number of the levels of concentration levels may be two or greater than two. Each of the levels of concentration may be within a dynamic detection range of a signal detector or sensor.

In some embodiments, the reference objects may be of near-homogeneous size ranging from 1 picoliter to 100 nanoliter.

In some embodiments, the assay droplets may be of near-homogeneous size ranging from 1 picoliter to 100 nanoliter.

In some embodiments, the reference objects and assay droplets may be introduced as a randomly or near randomly interspersed mixture in the microfluidic device with a droplet-to-reference-object ratio ranging from about 3000:1 to about 1:5.

In some embodiments, the assay droplets may further include a low yet detectable level of a reference material that serves to facilitate enumeration of individual assay droplets.

In some embodiments, in collecting the signal data, process 1000 may involve optical detection of a fluorescent or luminescent signal from the assay droplets in the microfluidic device.

In some embodiments, in collecting the signal data, process 1000 may involve optical detection of a fluorescent signal, a bright-field signal, a scattering-light signal, or a combination thereof, from the reference objects in the microfluidic device.

In some embodiments, in collecting the signal data, process 1000 may involve magnetic field detection of magnetic or para-magnetic particles in the reference objects in the microfluidic device.

In some embodiments, the respective position index for one of the assay droplets may include: (a) an identifier representing one, two or more leading strings of tandem droplets immediately ahead of a residence string that contains the respective assay droplet along a flow direction; and (b) an identifier representing an intra-string position numbering of the respective assay droplet.

In some embodiments, the respective position index for one of the assay droplets may include: (a) an identifier representing at least one leading droplet-string ahead of a residence string that contains the respective assay droplet along a flow direction; (b) an identifier representing at least one lagging droplet-string behind; and (c) an identifier representing an intra-string position numbering of the respective assay droplet.

In some embodiments, the sorter device may be based on a dielectrophoretic (DEP), an acoustic, a microvalve, a piezoelectric, a dynamic stream deflection, or an electrical capacitance method.

In some embodiments, the sorter device may be activated by an upstream signal trigger with guidance of the respective position index of each of the selected assay droplets.

In some embodiments, the reference objects may be generated on-demand in the microfluidic device or provided from a stock as an off-the-shelf reagent.

FIG. 11 illustrates an example process 1100 in accordance with an implementation of the present disclosure. Process 1100 may represent an aspect of implementing the proposed concepts and schemes such as one or more of the various schemes, concepts and examples described above with respect to FIG. 1A-FIG. 9B. More specifically, process 1100 may represent an aspect of the proposed concepts and schemes pertaining to reference-assisted kinetic detection, indexing and sorting of droplets for assays and diagnostics. Process 1100 may include one or more operations, actions, or functions as illustrated by one or more of blocks 1110, 1120, 1130 and 1140. Although illustrated as discrete blocks, various blocks of process 1100 may be divided into additional blocks, combined into fewer blocks, or eliminated, depending on the desired implementation. Moreover, the blocks of process 1100 may be executed in the order shown in FIG. 11 or, alternatively in a different order. Furthermore, the blocks of process 1100 may be executed iteratively. Process 1100 may begin at block 1110.

At 1110, process 1100 may involve introducing into a microfluidic device a plurality of water-in-oil droplets that comprise a plurality of assay droplets, as assay samples, and a plurality of reference objects that contain at least one kind of a reference material. The reference objects and assay droplets may be interspersed in a single-stream manner or a multiple single-streams manner in the microfluidic device. Process 1100 may proceed from 1110 to 1120.

At 1120, process 1100 may involve collecting signal data representing signals from individual reference objects of the plurality of reference objects and from individual assay droplets of the plurality of assay droplets in the microfluidic device at two or more time-points over a period. Process 1100 may proceed from 1120 to 1130.

At 1130, process 1100 may involve processing the collected signal data to identify the individual reference objects and the individual assay droplets, and to generate a respective position index for each of the individual assay droplets by using two or more proximal reference objects of the plurality of reference objects as a position reference. The respective position index for one of the individual assay droplets may be unchanged or largely unchanged over a first predefined period of time. Process 1100 may proceed from 1130 to 1140.

At 1140, process 1100 may involve establishing respective assay-signal kinetics for each of the individual assay droplets over a second predefined period of time. A number of the assay droplets with a predefined kinetics property may be accordingly identified from a total droplet population of the plurality of assay droplets.

Highlights of Selected Features

In view of the above, select features in accordance with the present disclosure are highlighted below.

In one aspect in accordance with the present disclosure, a method for detection, indexing and sorting of droplets may involve the following: (a) introducing into a microfluidic device a plurality of water-in-oil droplets that comprise a plurality of assay droplets, as assay samples, and a plurality of reference objects that contain at least one reference material, with the reference objects and assay droplets being interspersed in a single-stream manner or a multiple single-streams manner in the microfluidic device; (b) collecting signal data representing signals from individual reference objects of the plurality of reference objects and from individual assay droplets of the plurality of assay droplets in the microfluidic device at two or more time-points over a period; (c) processing the collected signal data to identify the individual reference objects and the individual assay droplets, and to generate a respective position index for each of the individual assay droplets by using two or more reference objects proximal to each of the individual assay droplets as a position reference for a given assay droplet of the assay droplets; (d) establishing a respective assay-signal kinetics for each of the individual assay droplets over a predefined period of time, with each of a number of assay droplets of the plurality of assay droplets with a respective kinetics property meeting a predefined condition being accordingly selected from a total droplet population of the plurality of assay droplets; and (e) sorting the selected assay droplets with a sorter device by using the respective position index of each of the selected assay droplets as a guide to generate a sorter-device activation signal.

In some embodiments, the assay droplets may contain a biological sample, a chemical sample, a food sample, a water sample, a forensic sample, an environmental sample, a derivative of one or more thereof, or a mixture of one or more thereof.

In some embodiments, the assay droplets may contain one or more kinds of light-emitting or light-absorbing substrates or reagents, which allow detection of optical signals as an assay readout.

In some embodiments, the assay droplets may contain one or more kinds of inducible or pre-provided fluorophore-containing reporter molecules, which allow detection of fluorescent signals as an assay readout.

In some embodiments, the reference objects may include water-in-oil droplets with a similar shape and size as that of the assay droplets in the microfluidic device. In some embodiments, the size of one of the reference objects may be similar to that of one of the assay droplets with a deviation of less than 60%. In some embodiments, and more preferably, the size of one of the reference objects may be similar to that of one of the assay droplets with a deviation of less than 20%.

In some embodiments, the reference objects may include a solid or liquid-solid-mixed object with a similar shape and size as that of the assay droplets in the microfluidic device. In some embodiments, the size of one of the reference objects may be similar to that of one of the assay droplets with a deviation of less than 60%. In some embodiments, and more preferably, the size of one of the reference objects may be similar to that of one of the assay droplets with a deviation of less than 20%.

In some embodiments, the reference material in the reference objects may include one or more kinds of fluorophore-containing materials selected from a group comprising chemicals, molecules, dyes, proteins, polymers, particles, barcodes and complexes. In some embodiments, and more preferably, the reference material in the reference objects may include a fluorophore-containing chemical, polymer or particle.

In some embodiments, the reference material in the reference objects may include one or more kinds of color-coded materials selected from a group comprising chemicals, dyes, particles, polymers, and barcodes. In some embodiments, and more preferably, the reference material in the reference objects may include a color-coded dye, barcode or particle.

In some embodiments, the reference material in at least one of the reference objects may include magnetic or para-magnetic particles. In some embodiments, the magnetic particles may have a size ranging from about 1 nm to about 30 µm. In some embodiments, and preferably, the magnetic particles may have a size ranging from about 30 nm to about 10 µm. In some embodiments, and more preferably, the magnetic particles may have a size ranging from about 50 nm to about 5 µm.

In some embodiments, the solid or liquid-solid-mixed reference object may include a support matrix of plastic polymers, organic polymers, glass, silicon, or gel-forming polymers or pre-polymers.

In some embodiments, the solid or liquid-solid-mixed reference object may include a soft-solid support matrix of a gel forming substrate comprising alginate, or hydrogel polymers or pre-polymers.

In some embodiments, the reference material in the reference objects may be of a serial level of concentrations. Alternatively, the reference material in the reference objects may be of a fixed or near fixed level. In some embodiments, the serial level of concentrations may range from 1 aM (attomolar) to 10 M (molar). In some embodiments, and preferably, the serial level of concentrations may range from 10 fM (femtomolar) to 1 M. In some embodiments, and more preferably, the serial level of concentrations may range from 1 nM (nanomolar) to 1 mM (millimolar).

In some embodiments, a number of the levels of concentration levels may be two or greater than two. In some embodiments, each of the levels of concentration may be within a dynamic detection range of a signal detector or sensor. In some embodiments, and preferably, the number of the levels of concentration levels may be two, three, four or no more than ten concentration levels. In some embodiments, and preferably, each of the levels of concentration may be resolved from other levels.

In some embodiments, the reference objects may be of near-homogeneous size ranging from 1 picoliter to 100 nanoliter. In some embodiments, and preferably, the reference objects may be of near-homogeneous size ranging from 10 picoliter to 10 nanoliter. In some embodiments, and more preferably, the reference objects may be of near-homogeneous size ranging from 30 picoliter to 1 nanoliter.

In some embodiments, the assay droplets may be of near-homogeneous size ranging from 1 picoliter to 100 nanoliter. In some embodiments, and preferably, the reference objects may be of near-homogeneous size ranging from 5 picoliter to 5 nanoliter. In some embodiments, and more preferably, the reference objects may be of near-homogeneous size ranging from 20 picoliter to 2 nanoliter.

In some embodiments, the reference objects and assay droplets may be introduced as a randomly or near randomly interspersed mixture in the microfluidic device with a droplet-to-reference-object ratio ranging from about 3000:1 to about 1:5. In some embodiments, and preferably, the droplet-to-reference-object ratio may range from about 200:1 to about 1:1. In some embodiments, and more preferably, the droplet-to-reference-object ratio may range from about 50:1 to about 5:1.

In some embodiments, the assay droplets may further include a low yet detectable level of a reference material that serves to facilitate enumeration of individual assay droplets.

In some embodiments, the collecting of the signal data may involve optical detection of a fluorescent or luminescent signal from the assay droplets in the microfluidic device.

In some embodiments, the collecting of the signal data may involve optical detection of a fluorescent signal, a bright-field signal, a scattering-light signal, or a combination thereof, from the reference objects in the microfluidic device.

In some embodiments, the collecting of the signal data may involve magnetic field detection of magnetic or para-magnetic particles in the reference objects in the microfluidic device.

In some embodiments, the respective position index for one of the assay droplets may include the following: (1) an identifier representing one, two or more leading strings of tandem droplets immediately ahead of a residence string that contains the respective assay droplet along a flow direction; and (2) an identifier representing an intra-string position numbering of the respective assay droplet.

In some embodiments, the respective position index for one of the assay droplets may include the following: (1) an identifier representing at least one leading droplet-string ahead of a residence string that contains the respective assay droplet along a flow direction; (2) an identifier representing at least one lagging droplet-string behind; and (3) an identifier representing an intra-string position numbering of the respective assay droplet.

In some embodiments, the sorter device may be based on a dielectrophoretic (DEP), an acoustic, a microvalve, a piezoelectric, a dynamic stream deflection, or an electrical capacitance method. In some embodiments, and preferably, the sorter device may be based on a DEP or acoustic method.

In some embodiments, the sorter device may be activated by an upstream signal trigger with guidance of the respective position index of each of the selected assay droplets.

In some embodiments, the reference objects may be generated on-demand in the microfluidic device or provided from a stock as an off-the-shelf reagent.

In one aspect in accordance with the present disclosure, a system for detecting, indexing, and sorting water-in-oil droplets may include the following: (a) a droplet and reference-object providing module that introduces a plurality of assay droplets and a plurality of reference objects as an interspersed mixture into a microfluidic device; (b) a signal detection and processing module that collects and processes signal data representing individual reference objects and assay droplets to generate respective position index for individual assay droplets by using two or more proximal reference objects of the plurality of reference objects as a position reference for a given assay droplet of the plurality of assay droplets, with the signal detection and processing module generating assay kinetics respectively for individual assay droplets over a predefined period of time to select a pool of droplets from the plurality of assay droplets with a predefined kinetics property; and (c) a droplet sorting module that retrieves the selected pool of droplets for further analysis or usage.

In some embodiments, the droplet and reference-object providing module may be capable of performing on-device generation and mixing of the reference objects with the assay droplets.

In some embodiments, the droplet and reference-object providing module may be capable of introducing the reference objects from an off-the-shelf stock.

In some embodiments, the microfluidic device may include a droplet-housing structure comprising a straight channel or tube, a curved channel or tube with various curvature features, or a channel or tube with both straight and curvature features. In some embodiments, the channel or tube may be configured to house a single stream comprising a droplet/reference-object mixture.

In some embodiments, the microfluidic device may include a droplet-housing structure comprising two or more channels or tubes that are configured to house a droplet/reference mixture arranged in parallel single-streams or multiple single-streams.

In some embodiments, the system may further include a droplet incubation module. In some embodiments, the signal detection and processing module may be integrated with the droplet incubation module. The droplet incubation module may include features selected from a group comprising a temperature control unit with a preferred temperature range of about 4° C.-98° C., an oxygen control unit with a preferred $O_2$ level of about 0.01%-30%, a carbon dioxide control unit with a preferred $CO_2$ level of about 0.1%-20%, and a humidity control unit with a preferred humidity level of about 50% to 99%.

In some embodiments, the signal detection and processing module may include a single detector that detects the signal data representing assay droplets and reference droplets. In some embodiments, the single detector may include an optical signal detector comprising a charge-coupled device (CCD) camera, a complementary metal oxide semiconductor sensor (CMOS), a photomultiplier (PMT), an avalanche photodiode (APD), or a combination thereof.

In some embodiments, the signal detection and processing module may include a first detector, that detects assay-readout signals from the assay droplets, and a second detector, that senses signals representing a reference material provided in one of the reference objects, one of the assay droplets, or both.

In some embodiments, the signal data collection and processing module may include a dedicated signal acquisition and processing board. In some embodiments, the signal acquisition and processing board may collect and process the signal data in a near real-time manner to render the respective position index for one of the assay droplets by using two or more proximal reference objects of the plurality of reference objects as a position reference map.

In some embodiments, the droplet sorting module may be based on a dielectrophoretic (DEP), an acoustic, a microvalve, a piezoelectric, a dynamic stream deflection, or an electrical capacitance mechanism, which is activated with guidance of the respective position index of each of the selected assay droplets. In some embodiments, and preferably, the droplet sorting module may be based on a DEP or acoustic method.

In some embodiments, the reference objects may include a fluorophore-containing or color-coded reference-material that is detectable using an optical detector.

In some embodiments, the reference objects may include a magnetic reference material that is detectable using a magnetic field sensor.

In one aspect in accordance with the present disclosure, a method for detecting and indexing droplets may involve the following: (a) introducing into a microfluidic device a plurality of water-in-oil droplets that comprise a plurality of assay droplets, as assay samples, and a plurality of reference objects that contain at least one kind of a reference material, with the reference objects and assay droplets being interspersed in a single-stream manner or a multiple single-streams manner in the microfluidic device; (b) collecting signal data representing signals from individual reference objects of the plurality of reference objects and from individual assay droplets of the plurality of assay droplets in the microfluidic device at two or more time-points over a period; (c) processing the collected signal data to identify the individual reference objects and the individual assay droplets, and to generate a respective position index for each of the individual assay droplets by using two or more proximal reference objects of the plurality of reference objects as a position reference, with the respective position index for one of the individual assay droplets being unchanged or largely unchanged over a first predefined period of time; and (d) establishing respective assay-signal kinetics for each of the individual assay droplets over a second predefined period of time, with a number of the assay droplets with a predefined kinetics property being accordingly identified from a total droplet population of the plurality of assay droplets.

Additional Notes

Although some embodiments are disclosed above, they are not intended to limit the scope of the present disclosure. It will be apparent to those skilled in the art that various modifications and variations can be made to the disclosed embodiments of the present disclosure without departing from the scope or spirit of the present disclosure. In view of the foregoing, the scope of the present disclosure shall be defined by the following claims and their equivalents.

What is claimed is:

1. A method for detection, indexing and sorting of droplets, comprising:
   introducing into a microfluidic device a plurality of water-in-oil droplets that comprise a plurality of assay droplets, as assay samples, and a plurality of reference objects that contain at least one reference material, wherein the reference objects and assay droplets are interspersed in a single-stream manner or a multiple-single-streams manner in the microfluidic device;
   collecting signal data representing signals from individual reference objects of the plurality of reference objects and from individual assay droplets of the plurality of assay droplets in the microfluidic device at two or more time-points over a period;
   processing the collected signal data to identify the individual reference objects and the individual assay droplets, and to generate a respective position index for each of the individual assay droplets by using two or more reference objects proximal to each of the individual assay droplets as a position reference for a given assay droplet of the assay droplets;
   establishing a respective assay-signal kinetics for each of the individual assay droplets over a predefined period of time, wherein each of a number of assay droplets of the plurality of assay droplets with a respective kinetics property meeting a predefined condition is accordingly selected from a total droplet population of the plurality of assay droplets; and
   sorting the selected assay droplets with a sorter device by using the respective position index of each of the selected assay droplets as a guide to generate a sorter-device activation signal.

2. The method of claim 1, wherein the assay droplets contain a biological sample, a chemical sample, a food sample, a water sample, a forensic sample, an environmental sample, a derivative of one or more thereof, or a mixture of one or more thereof.

3. The method of claim 1, wherein the reference objects comprise water-in-oil droplets with a similar shape and size as that of the assay droplets in the microfluidic device, and wherein the size of one of the reference objects is similar to that of one of the assay droplets with a deviation of less than 60%.

4. The method of claim 1, wherein the reference objects comprise a solid or liquid-solid-mixed object with a similar shape and size as that of the assay droplets in the microfluidic device, and wherein the size of one of the reference objects is similar to that of one of the assay droplets with a deviation of less than 60%.

5. The method of claim 1, wherein the reference material in the reference objects comprises one or more kinds of fluorophore-containing materials selected from a group comprising chemicals, molecules, dyes, proteins, polymers, particles, barcodes and complexes.

6. The method of claim 1, wherein the reference material in at least one of the reference objects comprises magnetic or para-magnetic particles, and wherein the magnetic particles have a size ranging from about 1 nm to about 30 μm.

7. The method of claim 1, wherein the reference material in the reference objects is of a serial level of concentrations, and wherein the serial level of concentrations ranges from 1 aM (attomolar) to 10 M (molar).

8. The method of claim 1, wherein the reference objects and assay droplets are introduced as a randomly or near randomly interspersed mixture in the microfluidic device with a droplet-to-reference-object ratio ranging from about 3000:1 to about 1:5.

9. The method of claim 1, wherein the respective position index for one of the assay droplets comprises:
   an identifier representing one, two or more leading strings of tandem droplets immediately ahead of a residence string that contains the respective assay droplet along a flow direction; and
   an identifier representing an intra-string position numbering of the respective assay droplet.

10. The method of claim 1, wherein the respective position index for one of the assay droplets comprises:
    an identifier representing at least one leading droplet-string ahead of a residence string that contains the respective assay droplet along a flow direction;
    an identifier representing at least one lagging droplet-string behind; and
    an identifier representing an intra-string position numbering of the respective assay droplet.

11. A system for detecting, indexing, and sorting water-in-oil droplets, comprising:
    a droplet and reference-object providing module that introduces a plurality of assay droplets and a plurality of reference objects as an interspersed mixture into a microfluidic device;
    a signal detection and processing module that collects and processes signal data representing individual reference objects and assay droplets to generate respective position index for individual assay droplets by using two or more proximal reference objects of the plurality of reference objects as a position reference for a given assay droplet of the plurality of assay droplets, wherein the signal detection and processing module generates assay kinetics respectively for individual assay droplets over a predefined period of time to select a pool of droplets from the plurality of assay droplets with a predefined kinetics property; and
    a droplet sorting module that retrieves the selected pool of droplets for further analysis or usage.

12. The system of claim 11, wherein the microfluidic device comprises a droplet-housing structure comprising a straight channel or tube, a curved channel or tube with various curvature features, or a channel or tube with both straight and curvature features, and wherein the channel or tube is configured to house a single stream comprising a droplet/reference-object mixture.

13. The system of claim 11, wherein the microfluidic device comprises a droplet-housing structure comprising two or more channels or tubes that are configured to house a droplet/reference mixture arranged in parallel single-streams or multiple single-streams.

14. The system of claim 11, wherein the signal detection and processing module comprises a single detector that detects the signal data representing assay droplets and reference droplets, wherein the single detector comprises an optical signal detector comprising a charge-coupled device (CCD) camera, a complementary metal oxide semiconductor sensor (CMOS), a photomultiplier (PMT), an avalanche photodiode (APD), or a combination thereof.

15. The system of claim 11, wherein the signal detection and processing module comprises a first detector, that detects assay-readout signals from the assay droplets, and a second detector, that senses signals representing a reference material provided in one of the reference objects, one of the assay droplets, or both.

16. The system of claim 11, wherein the signal data collection and processing module comprises a dedicated signal acquisition and processing board, and wherein the signal acquisition and processing board collects and processes the signal data in a near real-time manner to render the respective position index for one of the assay droplets by using two or more proximal reference objects of the plurality of reference objects as a position reference map.

17. The system of claim 11, wherein the droplet sorting module is based on a dielectrophoretic (DEP), an acoustic, a microvalve, a piezoelectric, a dynamic stream deflection, or an electrical capacitance mechanism, which is activated with guidance of the respective position index of each of the selected assay droplets.

18. The system of claim 11, wherein the reference objects comprise a fluorophore-containing or color-coded reference-material that is detectable using an optical detector.

19. The system of claim 11, wherein the reference objects comprise a magnetic or paramagnetic reference material that is detectable using a magnetic field sensor.

20. A method for detecting and indexing droplets, comprising:
  introducing into a microfluidic device a plurality of water-in-oil droplets that comprise a plurality of assay droplets, as assay samples, and a plurality of reference objects that contain at least one kind of a reference material, wherein the reference objects and assay droplets are interspersed in a single-stream manner or a multiple single-streams manner in the microfluidic device;
  collecting signal data representing signals from individual reference objects of the plurality of reference objects and from individual assay droplets of the plurality of assay droplets in the microfluidic device at two or more time-points over a period;
  processing the collected signal data to identify the individual reference objects and the individual assay droplets, and to generate a respective position index for each of the individual assay droplets by using two or more proximal reference objects of the plurality of reference objects as a position reference, wherein the respective position index for one of the individual assay droplets is unchanged or largely unchanged over a first predefined period of time; and
  establishing respective assay-signal kinetics for each of the individual assay droplets over a second predefined period of time, wherein a number of the assay droplets with a predefined kinetics property are accordingly identified from a total droplet population of the plurality of assay droplets.

* * * * *